(12) United States Patent
Oommen et al.

(10) Patent No.: US 10,927,402 B2
(45) Date of Patent: Feb. 23, 2021

(54) CAPSULE FOR LYOPHILIZED REAGENT STORAGE AND DELIVERY

(71) Applicant: Stem Arts Projects, LLC, Lincoln, NE (US)

(72) Inventors: Abraham Oommen, Lincoln, NE (US); Heather Piscatelli, Lincoln, NE (US); Molly Manning, Lincoln, NE (US); Alyssa Hangman, Lincoln, NE (US)

(73) Assignee: STEM Arts Projects, LLC, Lincoln, NE (US)

( * ) Notice: Subject to any disclaimer, the term of this patent is extended or adjusted under 35 U.S.C. 154(b) by 61 days.

(21) Appl. No.: 15/949,985

(22) Filed: Apr. 10, 2018

(65) Prior Publication Data

US 2019/0309344 A1 Oct. 10, 2019

(51) Int. Cl.
C12Q 1/68 (2018.01)
C12Q 1/6806 (2018.01)
C12Q 1/6848 (2018.01)

(52) U.S. Cl.
CPC ......... *C12Q 1/6806* (2013.01); *C12Q 1/6848* (2013.01)

(58) Field of Classification Search
CPC .............................. C12Q 1/6806; C12Q 1/6848
See application file for complete search history.

(56) References Cited

U.S. PATENT DOCUMENTS

| 4,515,753 A | 5/1985 | Smith et al. |
| 9,057,674 B2 * | 6/2015 | Van Atta ............... A61B 5/0059 |
| 2006/0051409 A1 | 3/2006 | Groenewoud |
| 2014/0058043 A1 * | 2/2014 | Miyamoto ........... C12Q 1/6846 525/289 |
| 2014/0271651 A1 | 9/2014 | Tu et al. |
| 2014/0315325 A1 | 10/2014 | Cobb |
| 2014/0356874 A1 | 12/2014 | Bearinger et al. |
| 2015/0126426 A1 | 5/2015 | Kumar et al. |
| 2015/0376692 A1 | 12/2015 | Esfandyarpour et al. |

FOREIGN PATENT DOCUMENTS

WO 98/52586 A1 11/1998

OTHER PUBLICATIONS

ISR/WO dated Jun. 14, 2019 for related application PCT/US19/26586, 13 pages.
EPO Extended European Search Report dated Nov. 24, 2020 for EP Patent Application No. 19784976.3, Including the European Search Opinion and Supplementary European Search Report completed Nov. 16, 2020, 7 pages.
Torpac Inc.: "Capsule Size Chart", Apr. 3, 2003 (Apr. 3, 2003), pp. 1-3, XP055750800, Retrieved from the Internet: URL:http://www.torpac.com/Reference/Torpac%20Size%20Chart.pdf [retrieved on Nov. 16, 2020].

* cited by examiner

*Primary Examiner* — David C Thomas
(74) *Attorney, Agent, or Firm* — AriAnna C. Goldstein; Baird Holm LLP

(57) ABSTRACT

A capsule to store and deliver lyophilized reagents is described. The lyophilized reagent capsule is configured to store a lyophilized reagent for at least five days, and is further configured to deliver a lyophilized reagent to a biological sample. The capsule includes a top, a bottom, and a lyophilized reagent. A method for delivering the lyophilized reagent via the capsule and without the use of pipettes to deliver the lyophilized reagents is described. The capsule may be part of a lyophilized reagent capsule kit.

19 Claims, 4 Drawing Sheets

100

CAPSULE FOR LYOPHILIZED REAGENT STORAGE AND DELIVERY

BACKGROUND

Proper storage and delivery of biological reagents for reactions is essential for successful reactions to produce accurate and precise results. Proper storage and delivery of biological reagents is hindered by two difficulties: stability of reagents during storage and transportation (collectively referred to as storage) and proper (e.g. accurate and precise) delivery of reagents to perform a reaction. Typically, biological reagents are required to be in liquid form for performance of a reaction. However, liquid biological reagents kept at room temperature (e.g. approximately 20-25 degrees Celsius) have a generally short longevity (e.g. longevity from a few hours to a few days), due to the photosensitivity, temperature sensitivity, or other environmental factors, that degrade the reagents. Degradation of a reagent compromises the ability to run a successful experiment, as well as adversely affecting the accuracy and precision of the reaction results. Storing liquid reagents increases stability (e.g. prevention of degradation) concerns as maintaining environmental factors that compromise stability are more difficult to control.

Conventional methods for storage of liquid biological reagents include refrigerating or freezing the biological reagents to maintain their stability. Refrigeration or freezing during storage is disadvantageous due to the necessity to maintain a consistent and low temperature. In particular, during the transportation phase of storage maintaining such consistent and low temperature is difficult, as it requires temperature controlled delivery methods (e.g. dry ice, insulated shipping containers, and the like) and time sensitive transport.

Other conventional methods of storing biological reagents include lyophilization of such reagents. Lyophilization of reagents increases stability of the reagent by eliminating or reducing environmental instability due to temperature sensitivity. Lyophilized reagents are typically stored by lyophilizing a single reagent in a reaction tube for further direct use by an end user.

Conventional methods for delivery of reagents in liquid form include the use of pipettes to ensure proper delivery to the biological reaction. The use of pipettes requires technical expertise to operate. Further, the use of pipettes may increase the time required to complete a biological reaction, as pipetting includes the need to calibrate and conduct the pipetting. Moreover, the use of pipettes are not conducive to utilization in a field scenario (e.g. on a farm, ranch, or at the point of care in an underserved area) and/or by an individual with little to no technical training.

Conventional methods for delivery of reagents in lyophilized form typically include rehydrating the single lyophilized reagent in the reaction tube it was stored within. The rehydrated reagent is subsequently used during the reaction either by adding the biological sample for analysis to the reaction tube or by adding the reagent to a different reaction vessel. If the biological reaction requires more than one reagent, each reagent requires rehydration and addition to the biological sample. Conventional methods using lyophilized reagents require the use of pipettes to rehydrate the lyophilized reagent and to add the biological sample to the reaction tube or to deliver the rehydrated reagent to a reaction vessel containing the biological sample. Conventional methods of delivering lyophilized reagents to perform reactions have the drawbacks associated with pipettes discussed in the foregoing paragraph.

As on-site analysis of biological samples gains popularity, there is a need to both store stabilized reagents and to reduce the technical expertise required to conduct biological reactions. It is therefore desirable to have a storage mechanism for biological reagents that stabilizes the reagents for at least five days and up to several months during transportation at variant temperatures. It is further desirable to have a delivery mechanism for the biological reagents that does not require the use of a pipette.

SUMMARY

In an aspect of the present invention a lyophilized reagent capsule to store and deliver lyophilized reagents, includes a capsule configured to store a lyophilized reagent, the capsule including a top, a bottom, and the lyophilized reagent, wherein the top is configured to receive the bottom to form an airtight seal and is from 6 to 13 millimeters in length, and wherein the bottom is configured to be received by the top to form an airtight seal and is from 10 to 22 millimeters in length, and wherein the lyophilized reagent is configured to be received by and resides within the capsule, and wherein the lyophilized reagent is configured to complete a biological reaction.

In another aspect of the present invention, a method for performing a biological reaction with a lyophilized reagent capsule without the use of pipettes includes predetermining a sample to perform a biological reaction via a lyophilized reagent capsule, wherein the lyophilized reagent capsule comprises a top, a bottom, and a lyophilized reagent configured to complete the biological reaction; delivering the lyophilized reagent to the sample to perform the biological reaction; and analyzing the completed biological reaction.

In another aspect of the present invention a lyophilized reagent capsule kit includes one or more lyophilized reagent capsules configured to store a lyophilized reagent, the capsule comprising a top, a bottom, and the lyophilized reagent; a packaging configured to store the one or more lyophilized reagent capsules; and instructions configured to detail a method for using the one or more lyophilized reagent capsules.

DETAILED DESCRIPTION

A capsule to store and deliver lyophilized reagents is described. The lyophilized reagent capsule is configured to store a lyophilized reagent for at least five days, and is further configured to deliver a lyophilized reagent to a biological sample. The capsule includes a top, a bottom, and a lyophilized reagent. A method for delivering the lyophilized reagent via the capsule is described. The capsule may be part of a lyophilized reagent capsule kit.

Figure 1:
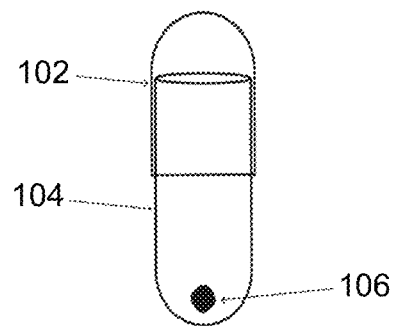
FIG. 1 represents a lyophilized reagent capsule.

FIG. 1 represents a lyophilized reagent capsule 100 configured to store and deliver a lyophilized reagent 106 to a biological sample. The lyophilized reagent capsule 100 includes a top 102, a bottom 104, and a lyophilized reagent 106. The lyophilized reagent capsule 100 is a length from 11 millimeters (mm) to 25 mm. Preferably, the capsule is 23.4 mm in length (e.g. size 00 within the capsule industry). The lyophilized reagent capsule 100 is configured to store the lyophilized reagent 106 for at least five days.

The top 102 of the lyophilized reagent capsule 100 may be configured to receive the bottom 104 of the lyophilized reagent capsule 100, such that an airtight seal (e.g. preventing air contaminants for reaching the inside of the lyophilized reagent capsule) is formed between the top 102 and the bottom 104. The top 102 of the lyophilized reagent capsule 100 may further be configured to be received by the bottom 104 of the lyophilized reagent capsule 100 to form an airtight seal. The top 102 has a length from 6 mm to 13 mm and a radius of 4 mm to 9 mm. The top 102 of the lyophilized reagent capsule 100 is made of a non-reactive material for storing and delivering the lyophilized reagent 106, such as gelatin or hypromellose (HPMC).

The bottom 104 of the lyophilized reagent capsule 100 may be configured to receive the top 102 of the lyophilized reagent capsule, such that an airtight seal is formed between the top 102 and the bottom 104. The bottom 104 of the lyophilized reagent capsule may further be configured to be received by the top 102 of the lyophilized reagent capsule to form an airtight seal. The bottom 104 has a length from 10 to 22 mm and a radius of 4 to 9 mm. The bottom 104 of the lyophilized reagent capsule 100 is made of a non-reactive material for storing and delivering the lyophilized reagent 106, such as gelatin or hypromellose (HPMC).

The lyophilized reagent 106 is configured to complete a biological reaction. The lyophilized reagent is one or more reagents needed to carry out a biological reaction to analyze an analyte of interest. The biological reaction may be deoxyribonucleic acid (DNA) amplification via polymerase chain reaction (PCR) amplification with fluorescence detection, DNA amplification via rolling circle amplification (RCA) with fluorescence detection, immunoassays, or another biological reaction for analysis of an analyte of interest. The analyte of interest may be any biological analyte, such as a gene mutation, an amino acid sequence, a bacterial pathogen, or an antigen. The lyophilized reagent is dehydrated as a pellet and is configured to be received by and reside within the lyophilized reagent capsule 100.

The lyophilized reagent 106 includes one or more lyophilized reagents necessary to complete a biological reaction, such that the addition of the lyophilized reagent to a biological sample delivers all of the necessary reagents for the particular biological reaction. For example, the lyophilized reagent 106 to carry out an immunoassay for a human bacterial pathogen would include a lyophilized fluorescent antibody. In another example, the lyophilized reagent 106 to carry out a nucleic acid detection reaction would include a DNA polymerase, DNA primers, and fluorescent DNA primers. The lyophilized reagent 106 includes a predetermined quantitative amount of lyophilized reagent 106 needed to conduct the reaction on a predetermined amount of biological sample, such that further measuring (such as by pipetting or the like) of the lyophilized reagent 106 is not required to perform the biological reaction.

Figure 2:
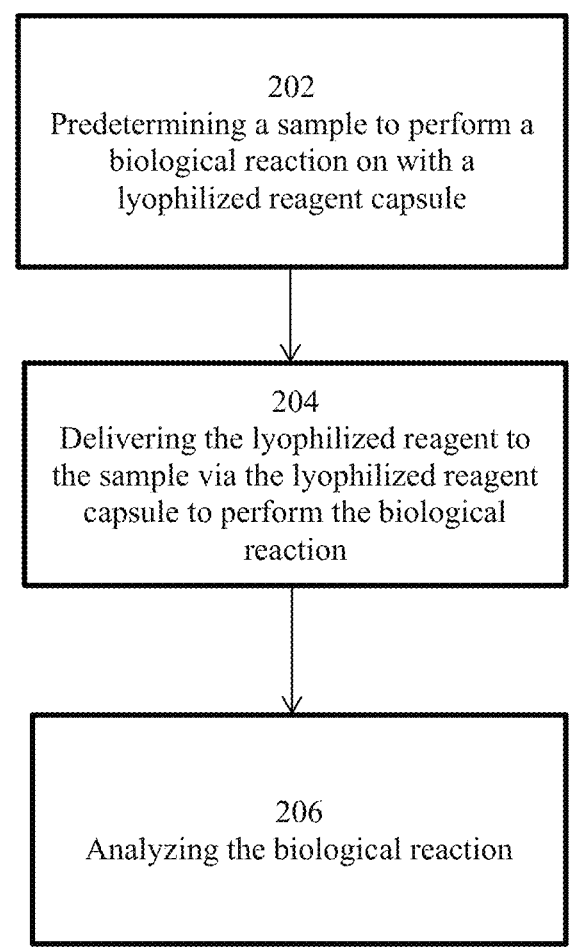
FIG. 2 depicts a method of delivering lyophilized reagent to a sample via a lyophilized reagent capsule.

FIG. 2 represents a method 200 for performing a biological reaction with a lyophilized reagent capsule. In 202 a sample is predetermined to perform a biological reaction on, with a lyophilized reagent capsule. The predetermining of the sample includes selecting the sample to be analyzed for the analyte of interest by the biological reaction carried out with the lyophilized reagent capsule. The predetermining of the sample may further include determining a sample volume needed for the biological reaction via the lyophilized reagent capsule. The sample volume may be from 10 microliter to 100 microliter. The predetermining of the sample may include delivering the sample volume which may be added to a reaction vessel via a pipette, a dropper bottle or other means of delivering liquid to a reaction.

In 204 a lyophilized reagent is delivered to the sample via the lyophilized reagent capsule to perform the biological reaction. The delivering includes opening the lyophilized reagent capsule, such as by removing a top of the lyophilized reagent capsule. The delivering may further include depositing the lyophilized reagent in a reaction tube, such as a 0.2 milliliter reaction tube within 10 minutes of opening the lyophilized reagent capsule. The reaction tube may contain the predetermined sample. The reaction tube may contain water or a buffer to rehydrate the lyophilized reagent and that may be needed for the biological reaction. The delivering may further include depositing the predetermined sample in the reaction tube having the lyophilized reagent. The delivering 204 further includes performance of the biological reaction when the lyophilized reagent contacts the sample. The biological reaction may be DNA amplification via PCR amplification with fluorescence detection, DNA amplification via RCA with fluorescence detection, immunoassays, or another biological reaction to analyze the analyte of interest.

In 206, the biological reaction is analyzed for the analyte of interest. Analyzing 206 may include fluorescence detection using conventional methods, when the biological reaction utilizes fluorescent labeled DNA primers, antibody-fluorophore conjugates, colorimetric reactions, or the like. The analyzing 206 may further include determining the presence or absence of the analyte of interest.

Figure 3:
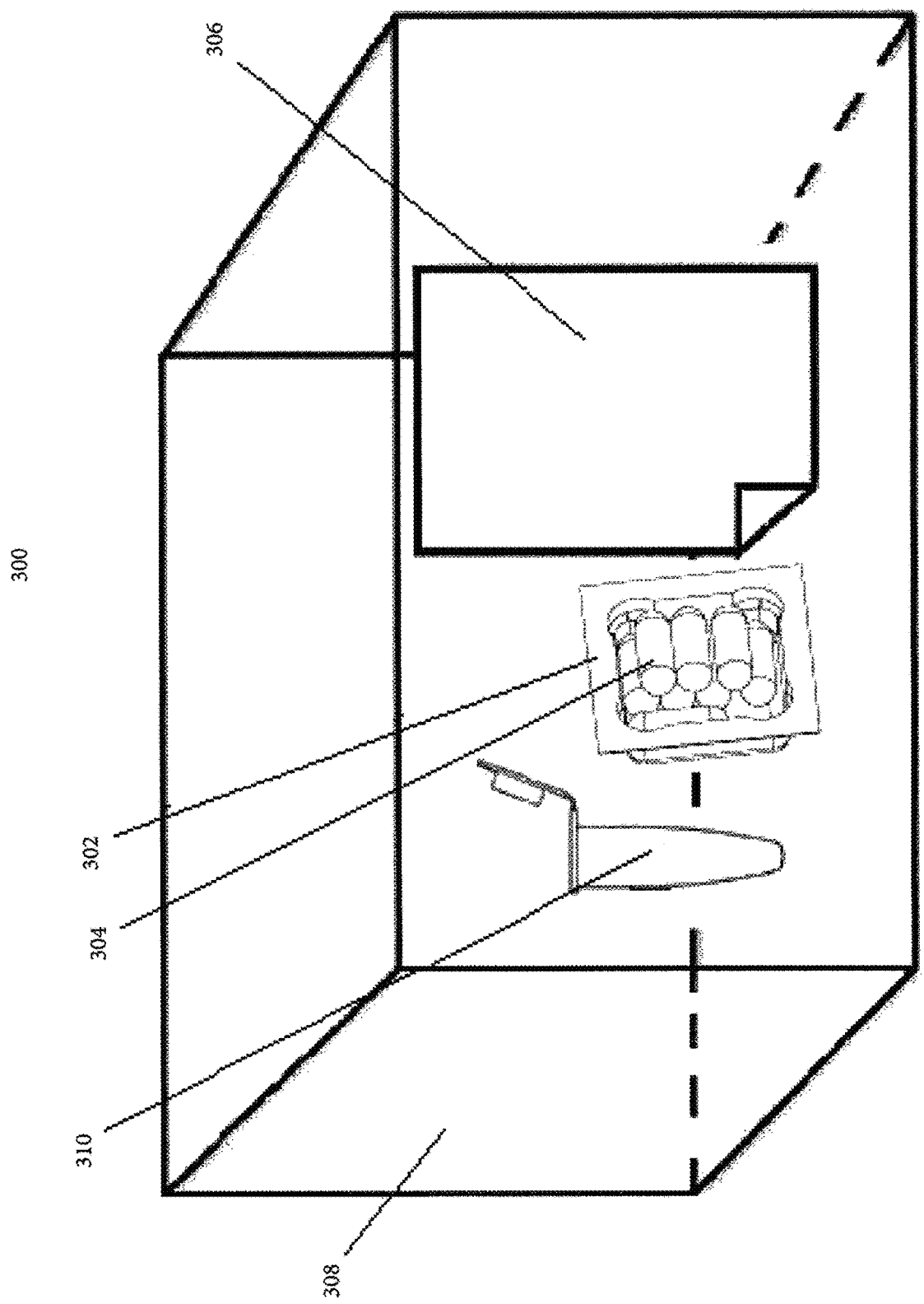
FIG. 3 represents a lyophilized reagent capsule kit to store lyophilized reagent capsules and to deliver lyophilized reagent to a biological sample.

FIG. 3 represents a lyophilized reagent capsule kit 300. The lyophilized reagent capsule may be a part of the lyophilized reaction capsule kit 300, which may be used in the field close to the source of a sample (e.g. cattle, swine, poultry, or humans) or in a laboratory. The lyophilized reagent capsule kit 300 includes one or more lyophilized reagent capsules 302, a packaging 304, and instructions 306. The lyophilized reagent capsule kit 300 also preferably includes a container 308. The lyophilized reagent capsule kit 300 may include at least one reaction tube 310.

The one or more lyophilized reagent capsules 302 are configured to store and deliver a lyophilized reagent to a biological sample. The one or more lyophilized reagent capsules 302 include a top, a bottom, and a lyophilized reagent configured to complete a biological reaction. The one or more lyophilized reagent capsules 302 may be stored in the packaging 304.

The packaging 304 is configured to store the one or more lyophilized reagent capsules to maintain the stability of the one or more lyophilized reagent capsules 302. When a lyophilized reagent of the lyophilized reagent capsule 302 is hygroscopic, the packaging is configured to minimize or prevent the absorption of moisture by the lyophilized reagent capsule 302, such as a vacuum sealed blister-pack, a bottle made of a non-reactive material containing a desiccant (e.g. silica, or the like), a bag made of a non-reactive material containing a desiccant, or by vacuum flushing and subsequently filling the packing with inert gas (e.g. nitrogen). When the lyophilized reagent of the lyophilized reagent capsule 302 is photosensitive (e.g. contains a fluorophore), the packaging 304 is configured to prevent light from reaching the lyophilized reagent, such as blister packs made of aluminum foil, opaque bottles made of a non-reactive material, or opaque bags made of a non-reactive material.

The instructions 306 are configured to detail a method for using the at least one lyophilized reagent capsule 302 in a biological reaction that the lyophilized reagent capsule 302 is configured to perform. The instructions 306 may include detail on performing the method of FIG. 2, such as 202, 204, and 206.

The at least one reaction tube 310 is configured to receive delivery of the lyophilized reagents of the at least one lyophilized reagent capsule 302 and is further configured to hold liquids and is made of a non-reactive material, such as glass, plastic, metal, polypropylene or ceramic. The at least one reaction tube 310 may further be configured to hold liquids when inverted, such as through a cap, lid, or rubber stopper.

The container 308 is configured to contain the at least one lyophilized reaction capsule 302, the packaging 304, and the instructions 306 and may further be configured to contain the at least one reaction tube 310 (collectively, the contents of the kit). The container 308 may be of any non-reactive material, such as cardboard, plastic, or polystyrene. The container 308 may be of any geometric shape configured for the holding the contents of the kit, such as a cuboid, cylinder, or triangular prism. The container 308 may further include a closure (not pictured) to keep the contents of the kit in the container 308 when inverted. The closure may be of any non-reactive material, such as cardboard, plastic, or polystyrene.

Figure 4A:
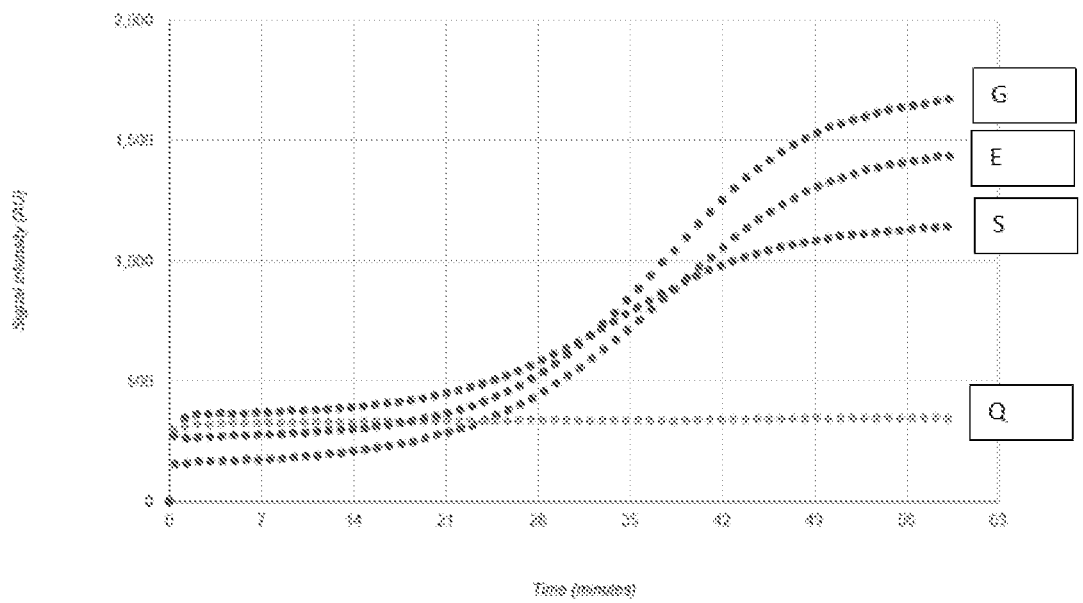
FIG. 4a and FIG. 4b represent a comparison of the efficacy of a biological reaction performed with lyophilized reagents delivered via a lyophilized reagent capsule, as shown in FIG. 4a versus a conventional method with liquid reagents, as shown in FIG. 4b.
Figure 4B:
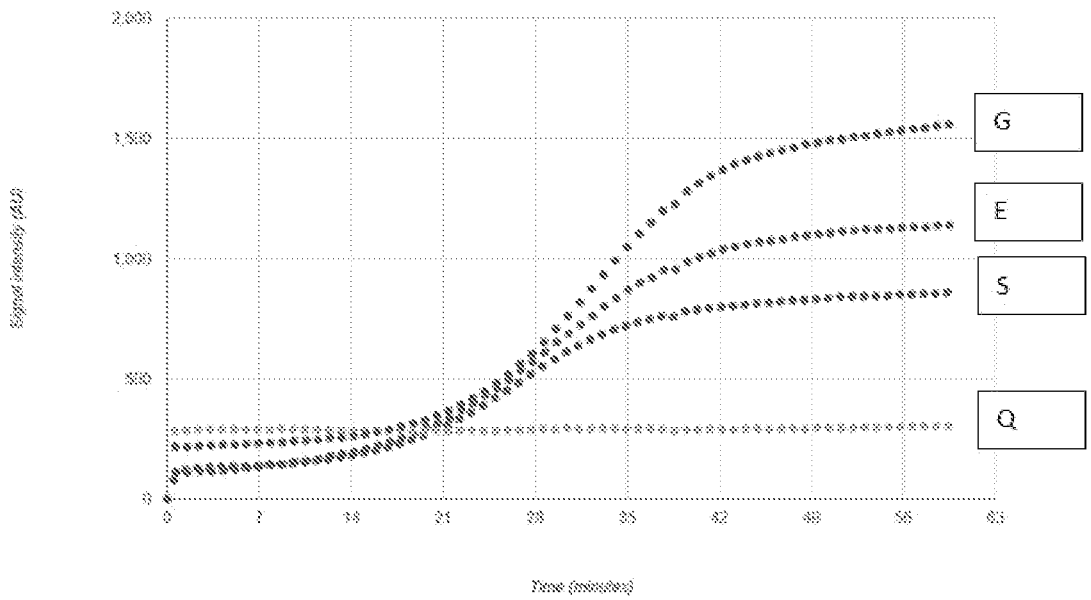

FIG. 4a and FIG. 4b represent a comparison of the efficacy of a biological reaction performed on a bovine DNA sample using a lyophilized reagent delivered via a lyophilized reagent capsule, as shown in FIG. 4a, versus performance with a conventional method having liquid reagents, as shown in FIG. 4b. The biological reaction for this comparison was detection of two bovine gene mutations (e.g. analyte of interest) via RCA and fluorescence detection. For FIG. 4a, a lyophilized reagent capsule configured to perform the biological reaction on the predetermined bovine DNA sample having lyophilized reagents of *Bacillus stearothermophilus* (Bst) DNA Polymerase, four primers for amplification of the analyte of interest via RCA, and four primers each with a different fluorophore.

The lyophilized reagent capsule was opened and the lyophilized reagents were delivered to a reaction vessel. The lyophilized reagents were rehydrated by adding a volume of water equal to approximately 30 microliters to dissolve the lyophilized reagents. The water was added using a dropper bottle. The bovine DNA sample was added to the reaction vessel by pipetting approximately 1 to 2 microliters of bovine DNA to the reaction vessel. The completed biological reaction was analyzed via fluorescence detection. FIG. 4a shows the fluorescence analyte detection as measured by signal intensity over time, where the letters "G", "E", "S", and "Q" identify the particular analytes detected.

For FIG. 4b, the liquid reagents of the conventional method included *Bacillus stearothermophilus* (Bst) DNA Polymerase, four primers for amplification of the analyte of interest via RCA, and four primers each with a different fluorophore in amounts configured to carry out the biological reaction on the predetermined sample of bovine DNA. The biological reaction was carried out with conventional methods utilizing pipettes for delivery of the liquid reagents. The completed biological reaction was analyzed via fluorescence detection. FIG. 4b shows the fluorescence analyte detection over time, where the letters "G", "E", "S", and "Q" identify the particular analytes detected.

As between the biological reaction carried out with the lyophilized reagents versus the conventional method, there was no statistically significant difference between the analyte detection (e.g. correct detection), indicating that the lyophilized reagents and delivery method work as well as conventional methods for detection of the analyte of interest in this comparative example.

The invention claimed is:

1. A lyophilized reagent capsule to store and deliver lyophilized reagents to a predetermined amount of a biological sample, comprising:
   a capsule configured to store a lyophilized reagent, the capsule comprising a top, a bottom, and the lyophilized reagent, wherein
      the top is configured to receive the bottom to form an airtight seal and is from 6 to 13 millimeters in length, and wherein
      the bottom is configured to be received by the top to form the airtight seal and is from 10 to 22 millimeters in length, and wherein
      the lyophilized reagent is configured to be received by and reside within the capsule, and wherein
      the lyophilized reagent comprises two or more reagents to complete a predetermined biological reaction in an amount configured to complete the predetermined biological reaction on the predetermined amount of the biological sample.

2. The capsule of claim 1, wherein
the capsule is from 11 to 25 millimeters in length.

3. The capsule of claim 1, wherein
the top has a radius from 4 to 9 millimeters, and wherein the bottom has a radius from 4 to 9 millimeters.

4. The capsule of claim 3, wherein
the top and the bottom are gelatin.

5. The capsule of claim 3, wherein
the top and the bottom are hypromellose.

6. The capsule of claim 5, wherein
the lyophilized reagent is configured to complete deoxyribonucleic acid amplification by polymerase chain reaction amplification having fluorescence detection.

7. The capsule of claim 5, wherein,
the lyophilized reagent is configured to complete deoxyribonucleic acid amplification by rolling circle amplification with fluorescence detection.

8. The capsule of claim 5, wherein
the lyophilized reagent is configured to complete an immunoassay by antigen detection.

9. A method for performing a predetermined biological reaction with a lyophilized reagent capsule without the use of pipettes to deliver a lyophilized reagents, comprising:
   predetermining a biological sample and a biological sample amount to perform a predetermined biological reaction via a lyophilized reagent capsule, where
      the lyophilized reagent capsule comprises a top, a bottom, and the lyophilized reagent, the lyophilized reagent comprising two or more reagents to complete the predetermined biological reaction in an amount configured to complete the predetermined biological reaction on the predetermined amount of the biological sample;
   delivering the lyophilized reagent to the biological sample to perform the biological reaction; and
   analyzing the completed biological reaction.

10. The method of claim 9, wherein
the delivering further comprises opening the lyophilized reagent capsule and depositing the lyophilized reagent in a reaction tube having the predetermined biological sample within ten minutes of opening the lyophilized reagent capsule.

11. The method of claim 9, wherein
the biological reaction is deoxyribonucleic acid amplification by polymerase chain reaction amplification having fluorescence detection.

12. The method of claim 10, wherein
the lyophilized reagent is configured to complete deoxyribonucleic acid amplification by rolling circle amplification with fluorescence detection.

13. The method of claim 10, wherein,
the lyophilized reagent is configured to complete an immunoassay by antigen detection.

14. A lyophilized reagent capsule kit, comprising:
one or more lyophilized reagent capsules configured to store a lyophilized reagent, the one or more lyophilized reagent capsules comprising a top, a bottom, and the lyophilized reagent, the lyophilized reagent comprising two or more reagents to complete a predetermined biological reaction in an amount configured to complete the predetermined biological reaction on a predetermined amount of a biological sample;
a packaging configured to store the one or more lyophilized reagent capsules;
instructions configured to detail a method for using the one or more lyophilized reagent capsules.

15. The kit of claim 14, further comprising:
at least one reaction tube configured to receive the lyophilized reagent; and
a container configured to contain the at least one lyophilized reagent capsule, the packaging, the instructions, and the at least one reaction tube.

16. The kit of claim 15, wherein
top and the bottom of the lyophilized reagent capsule are gelatin, and wherein
the lyophilized reagents is configured to perform the biological reaction selected from the group consisting of deoxyribonucleic acid amplification by polymerase chain reaction amplification having fluorescence detection, deoxyribonucleic acid amplification by rolling circle amplification with fluorescence detection, an immunoassay by antigen detection.

17. The capsule of claim 3, wherein
top and the bottom of the lyophilized reagent capsule are hypromellose, and wherein
the lyophilized reagents is configured to perform the biological reaction selected from the group consisting of deoxyribonucleic acid amplification by polymerase chain reaction amplification having fluorescence detection, deoxyribonucleic acid amplification by rolling circle amplification with fluorescence detection, an immunoassay by antigen detection.

18. The kit of claim 16, wherein
the packaging is further configured to minimize absorption of moisture by the lyophilized reagent capsule.

19. The kit of claim 17, wherein
the packaging is further configured to prevent light from reaching the lyophilized reagent.

* * * * *